US009734282B2

(12) United States Patent
Melrose et al.

(10) Patent No.: US 9,734,282 B2
(45) Date of Patent: *Aug. 15, 2017

(54) BIOLOGICAL DATASET PROFILING OF CARDIOVASCULAR DISEASE AND CARDIOVASCULAR INFLAMMATION

(75) Inventors: Jennifer Melrose, Burlingame, CA (US); Elen Rosler, Burlingame, CA (US); Melissa Fischer, Jacksonville, OR (US); Sylvie Privat, Burlingame, CA (US); Eric J. Kunkel, San Mateo, CA (US); Ellen Berg, Palo Alto, CA (US)

(73) Assignee: DISCOVERX CORPORATION, Fremont, CA (US)

( * ) Notice: Subject to any disclaimer, the term of this patent is extended or adjusted under 35 U.S.C. 154(b) by 1791 days.

This patent is subject to a terminal disclaimer.

(21) Appl. No.: 11/910,200

(22) PCT Filed: Mar. 28, 2006

(86) PCT No.: PCT/US2006/011383
§ 371 (c)(1),
(2), (4) Date: May 30, 2008

(87) PCT Pub. No.: WO2006/105147
PCT Pub. Date: Oct. 5, 2006

(65) Prior Publication Data
US 2009/0118133 A1  May 7, 2009

Related U.S. Application Data

(60) Provisional application No. 60/666,019, filed on Mar. 28, 2005.

(51) Int. Cl.
| G01N 33/53 | (2006.01) |
| G01N 33/567 | (2006.01) |
| G06F 19/18 | (2011.01) |
| G06F 19/00 | (2011.01) |
| G06F 19/12 | (2011.01) |
| G06F 19/24 | (2011.01) |

(52) U.S. Cl.
CPC ............ *G06F 19/18* (2013.01); *G06F 19/704* (2013.01); *G06F 19/12* (2013.01); *G06F 19/24* (2013.01)

(58) Field of Classification Search
CPC ................................. G01N 33/50; G06F 19/10
See application file for complete search history.

(56) References Cited

U.S. PATENT DOCUMENTS

| 6,656,695 B2 | 12/2003 | Berg et al. |
| 6,716,588 B2 | 4/2004 | Sammak et al. |
| 6,763,307 B2 | 7/2004 | Berg et al. |
| 6,801,859 B1 * | 10/2004 | Friend et al. .................. 702/19 |
| 2002/0110840 A1 | 8/2002 | Tomai et al. |
| 2003/0087273 A1 | 5/2003 | Holzmayer et al. |
| 2003/0124524 A1 | 7/2003 | Kornman et al. |
| 2003/0138811 A1 | 7/2003 | Plavec et al. |
| 2003/0143520 A1 | 7/2003 | Hood et al. |

FOREIGN PATENT DOCUMENTS

| WO | 2004/087044 A2 | 10/2004 |
| WO | 2004/094609 A2 | 11/2004 |
| WO | 2004/094992 A2 | 11/2004 |
| WO | 2005/023987 A2 | 3/2005 |

OTHER PUBLICATIONS

Rice et al. Development of a High Volume Screen to Identify Inhibitors of Endothelial Cell Activation. Anal. Biochemistry. vol. 241, pp. 254-259, 1996.*
Born et al. J Physiol. (1963), 168, pp. 178-195.*
Hawrylowicz et al. J. Exp. Med., 174, 785-790, 1991.*
Louwrens et al (European journal of vascular and endovascular surgery, 1995, vol. 10, No. 3, pp. 289-293) See Abstract, Database Medline AN 1996000108.*
Wada et al. (International journal of molecular medicine, (Nov. 2001) vol. 8, No. 5, pp. 561-566) See Abstract, Database Medline AN 2001558001.*
May et al (Circulation, 2002, vol. 106, No. 16, pp. 2111-2117); see Abstract in Database Medline, AN 2002621944.*
Miller (Journal of leukocyte biology, 1998, vol. 63, No. 3, pp. 373-379); see Abstract in Database Medline, AN 1998160162.*
Anker et al., "How to Recover from Renaissance? The significance of the results of Recover, Renaissance, Renewal and Attach", International Journal of Cardiology, 2002, 86:123-130.
Cousin, "Withdrawal of Vioxx Casts a Shadow Over COX-2 Inhibitors", Science, Oct. 14, 2004, 306:384-385.
McCarey; et al., "Trial of Atorvastatin in Rheumatoid Arthritis (TARA): double-blind, randomised placebo-controlled trial", The Lancet, Jun. 19, 2004, 363:2015-2021.
Heller, et al., "Discovery and analysis of inflammatory disease-related genes using cDNA microarrays", Proceedings of the National Academy of Sciences of USA, vol. 94, Mar. 1997, pp. 2150-2155.
CIPO Office Action dated Feb. 14, 2012, CA Appl. No. 2,400,989, 5 pp.
Monks, et al., "The NCI anti-cancer drug screen: a smart screen to identify effectors of novel targets", Anti-Cancer Drug Design, 12, 1997, pp. 553-541.
EPO Search Report dated Dec. 9, 2009, EP Appl. No. 06739889.1, 8 pp.
EPO Exam Report dated Apr. 23, 2014, EP Appl. No. 06739889.1, 15 pp.

(Continued)

Primary Examiner — Michael Borin
(74) Attorney, Agent, or Firm — Brian E. Davy; Bozicevic, Field & Francis LLP

(57) ABSTRACT

Methods and systems for evaluating biological dataset profiles relating to inflammatory cardiovascular conditions are provided, where datasets comprising information for multiple cellular parameters are compared and identified, and used in the evaluation of candidate pharmacologic agents for suitability as therapeutic agents.

6 Claims, 4 Drawing Sheets

(56) References Cited

OTHER PUBLICATIONS

Konstantopoulos, et al., "Endothelial P-selectin and VCAM-1 each can function as primary adhesive mechanisms for T cells under conditions of flow", Journal of Leukocyte Biology, vol. 61, Feb. 1997, pp. 179-187.

Butcher, et al., "Systems biology in drug discovery," Nature Biotechnology, vol. 22, No. 10, Oct. 2014, pp. 1253-1259.

Kunkel, et al., "An integrative biology approach for analysis of drug action in models of human vascular inflammation," The FASEB Journal express article 10.1096/fj.04-1538fje., Published online Jun. 18, 2004, 21 pp.

Kunkel, et al., "Rapid Structure-Activity and Selectivity Analysis of Kinase Inhibitors by BioMAP Analysis in Complex Human Primary Cell-Based Models," Assay and Drug Development Technologies, 2004, vol. 2, No. 4, pp. 431-441.

\* cited by examiner

Figure 1. BioMAP Profile for lovastatin
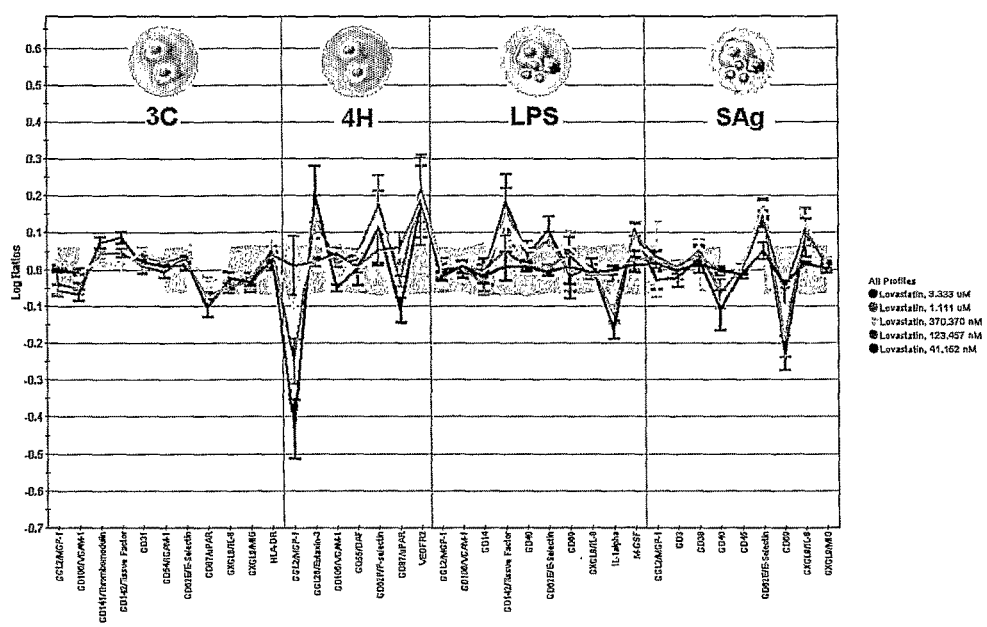

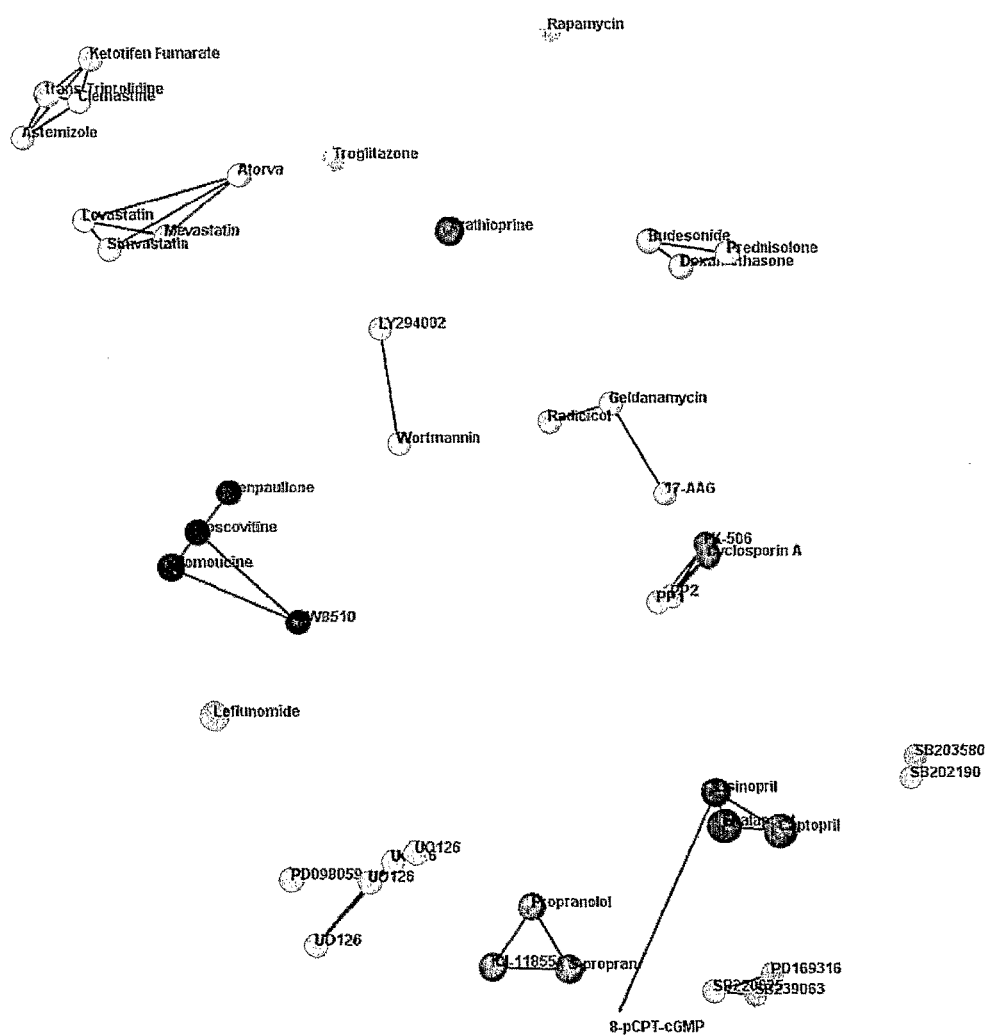
Figure 2. Function similarity map of compounds based on BioMAP profiles in 3C, 4H, LPS and SAg systems.

Figure 3. BioMAP profile of atorvastatin in the SM3C system.
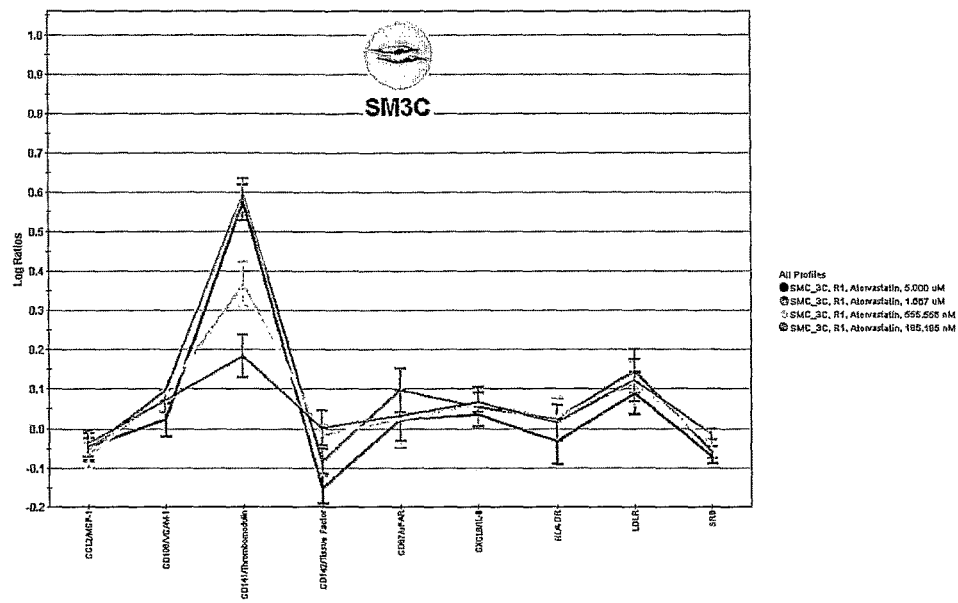
Figure 4. BioMAP of atorvastatin in the Mphg system
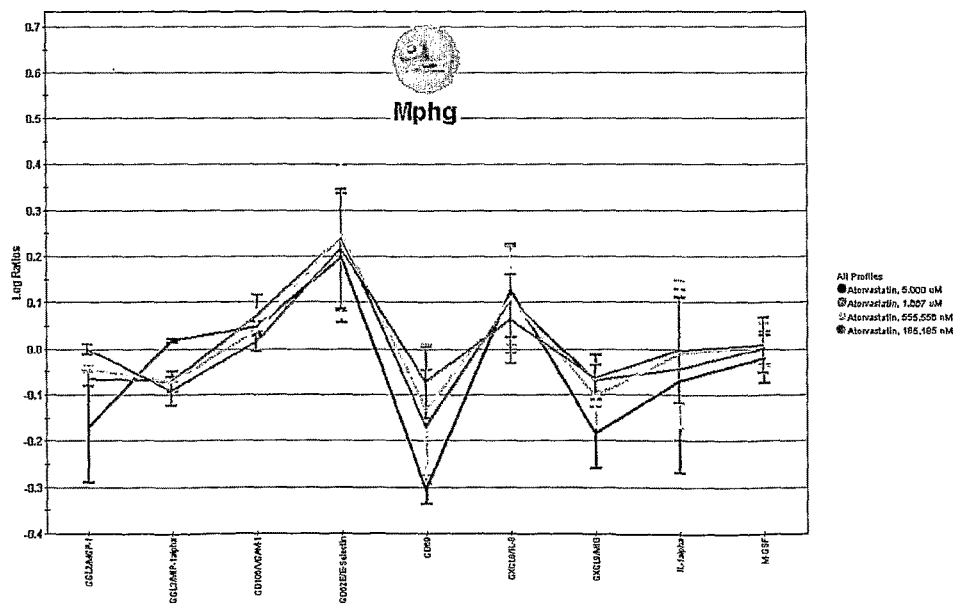

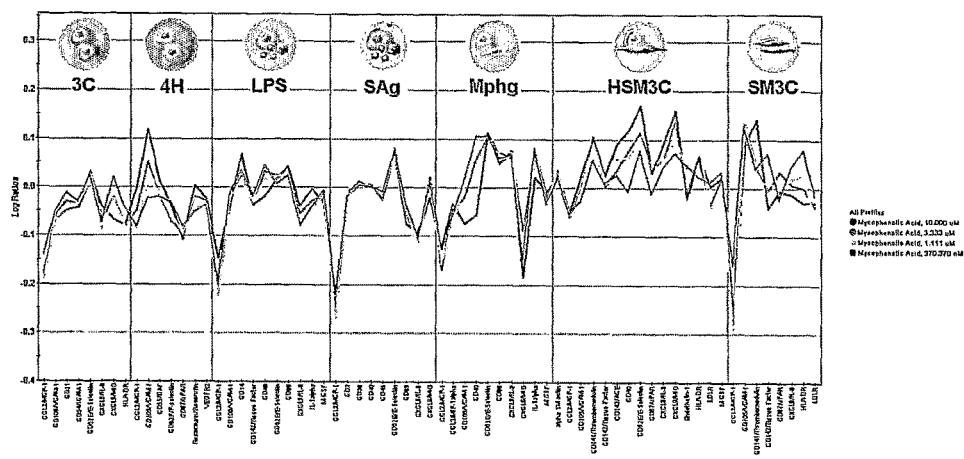
Figure 5. Mycophenolic Acid in multiple BioMAP systems

BIOLOGICAL DATASET PROFILING OF CARDIOVASCULAR DISEASE AND CARDIOVASCULAR INFLAMMATION

FIELD OF THE INVENTION

The field of the invention is the discrimination between different cellular pathways and their use in the determination of the effect of agents on conditions of cardiovascular inflammation.

BACKGROUND

Knowledge of the biochemical pathways by which cells detect and respond to stimuli is important for the discovery, development, and correct application of pharmaceutical products. Cellular physiology involves multiple pathways, which have complex relationships. For example, pathways split and join; there are redundancies in performing specific actions; and response to a change in one pathway can modify the activity of another pathway, both within and between cells. In order to understand how a candidate agent is acting and whether it will have the desired effect, the end result, and effect on pathways of interest is as important as knowing the target protein.

BioMAP® methods of analysis for determining the pathways affected by an agent or genotype modification in a cell, and for identifying common modes of operation between agents and genotype modifications, are described in International Patent application WO01/067103. Cells capable of responding to factors, simulating a state of interest are employed. Preferably the cells are primary cells in biologically relevant contexts. A sufficient number of factors are employed to involve a plurality of pathways and a sufficient number of parameters are selected to provide an informative dataset. The data resulting from the assays can be processed to provide robust comparisons between different environments and agents.

Among physiological states of interest are cardiovascular conditions. These conditions, including hypertension, atherosclerosis, and chronic heart failure affect more than 20% of the human population. Other conditions include angina, cardiac arrhythmia, cardiomyopathy, chronic venous insufficiency, diabetes, heart attack, high cholesterol, high homocysteine, high triglycerides, insulin resistance syndrome, and stroke. Inflammation has been associated with cardiovascular disease in several epidemiological studies, and the risk death from coronary disease has been shown to positively associate with elevated levels of inflammation markers, such as C-reactive protein (CRP), neopterin, matrix metalloproteinase-9 (MMP-9) and soluble intercellular adhesion molecules (sICAM).

Inflammatory cells, such as T cells, macrophages, etc., and inflammatory pathways, such as the NF-κB pathway, therefore contribute to the pathology of cardiovascular conditions. Inflammatory leukocyte trafficking into target tissues, e.g. atherosclerotic plaques, etc., and inflammatory mediators, e.g. cytokines, isoprenoids, etc. can affect cardiovascular processes including blood flow, vasoconstriction/dilation, and metabolic energy production.

However, while the cardiovascular stain drugs have been shown to have some immunomodulatory activities (see McCarey et al. (2004) Lancet 2004 363:2015-21), strategies to employ anti-inflammatory therapeutics for cardiovascular conditions have often met with failure (see Anker and Coats (2002) Int J Cardiol. 86:123-30; and Couzin (2004) Science 306:384-5).

Given the large number of cells and pathways involved in the development of cardiovascular inflammation, the evaluation of therapeutic modalities requires a complex assessment of effectiveness in multiple systems. The present invention addresses these issues.

SUMMARY OF THE INVENTION

The present invention provides methods and systems for evaluating biological dataset profiles relating to cardiovascular inflammation where datasets comprising information for multiple cellular parameters are compared and identified, and used in the evaluation of candidate pharmacologic agents for suitability as therapeutic agents. A typical dataset comprises readouts from multiple cellular parameters resulting from exposure of cells to biological factors in the absence or presence of a candidate agent, where the agent may be a chemical agent, e.g. drug candidate; or genetic agent, e.g. expressed coding sequence. Datasets may include control datasets, and/or profile datasets that reflect the parameter changes of known agents. Known agents may include those having acceptable therapeutic activities against cardiovascular disease states as well as those exemplifying undesirable side effects. For analysis of multiple context-defined systems, the output data from multiple systems may be concatenated.

In one embodiment of the invention, the biological dataset profile includes one or more cardiovascular disease associated cell systems. Cells associated with cardiovascular disease include endothelial cells, smooth muscle cells, blood leukocytes, platelets, macrophages, fibroblasts, mast cells, adipocytes, skeletal muscle cells and the like.

BRIEF DESCRIPTION OF THE DRAWING

FIG. 1. BioMAP profile of the HMG-CoA reductase inhibitor lovastatin in 4 systems, 3C, 4H, LPS and SAg. Readout parameters are listed on the x-axis. The log expression ratio of protein levels (ELISA OD units) from drug-treated, versus buffer control is shown on the y-axis. Key features of the atorvastatin profile include significant decreases in uPAR, MCP-1, IL-1alpha and CD69 in the 3C, 4H, LPS and SAg systems, respectively, and increases in Eotaxin-3 and P-selectin in the 4H system, tissue factor and M-CSF in the LPS system and E-selectin and IL-8 in the SAg system. Data shown are mean+/−SEM from 3 experiments (total n=9).

FIG. 2. Relationship of BioMAP profiles from multiple drug classes. Compounds were tested in 4 systems and BioMAP profiles analyzed as described. Compounds with the same mechanism of action have the same color. Compounds, their mechanism of action (target), and concentration tested are as follows:

FIG. 3. Biomap profile of atorvastatin in SMC3C system.

FIG. 4. BioMAP profile of atorvastatin in the ECZym system.

FIG. 5. Biomap profile of the IMPDH inhibitor, mycophenolic acid in multiple BioMAP systems.

DETAILED DESCRIPTION OF EMBODIMENTS

The inventive methods and compositions provide a system for the assessment of candidate therapies for cardiovascular disease, including hypertension, atherosclerosis, thrombosis, stroke, myocardial infarction, and diabetes.

Datasets of information are obtained from biologically multiplexed activity profiling (BioMAP®) of agents that are candidates for the treatment or involvement of cardiovascular disease. Such methods are described, for example, in U.S. Pat. No. 6,656,695 and U.S. Pat. No. 6,763,307; in co-pending U.S. patent application Ser. Nos. 10/220,999; 10/236,558; 10/716,349; and 10/856,564. Methods of analysis for such profiles are described in International application PCT/US2004/012688. Each of these documents are herein specifically incorporated by reference. Briefly, the methods provide screening assays for biologically active agents, where the effect of altering the environment of cells in culture is assessed by monitoring multiple output parameters. The result is a dataset that can be analyzed for the effect of an agent on a signaling pathway, for determining the pathways in which an agent acts, for grouping agents that act in a common pathway, for identifying interactions between pathways, and for ordering components of pathways.

Incorporating human biology early in drug development can improve the quality of drug targets and leads and reduce the frequency of compound attrition downstream. Screening methods of interest utilize a systems approach to characterization of drug function based on statistical analysis of protein expression data sets from multiple primary human cell-based disease systems. In these models, biological complexity is provided by the activation of multiple signaling pathways; interactions of multiple primary human cell types; and/or the use of multiple systems for data analysis. These model systems are surprisingly robust, reproducible, and responsive to and discriminatory of the activities of a large number of approved and investigational therapeutic agents.

In order to analyze agents that modulation inflammatory processes, particularly those of relevance to cardiovascular disease, model systems containing endothelial cells, smooth muscle cells, cardiac myocytes, peripheral blood cells, platelets, fibroblasts, mast cells etc. are used. The multi-cell and/or multifactor design of the systems and their analysis through multi-parameter activity profiles work together to optimize information content, enabling rapid but effective analysis of drug and gene target activities in complex cellular responses relevant to clinical disease.

Systems may utilize combinations of cells that are informative of the disease processes, e.g. a combination of cardiac myocyte and mononuclear peripheral blood cells; endothelial cells and smooth muscle cells; endothelial cells and monocytes; etc. Cells may be primary cultures or cell lines; and may be from normal tissues or from diseases tissues, e.g. peripheral blood monocytes from diabetic patients may be of interest; endothelial cells from restenotic patients, and the like. In some embodiments, combinations of exogenous factors are provided to simulate disease conditions, e.g. VEGF in combination with inflammatory factors; etc.

In coronary artery disease, atherosclerosis, also called "hardening of the arteries," occurs when fatty substances build up in the artery wall, making the artery stiffer than normal and causing partial or complete blockage of the flow of blood and oxygen to the body. Atherosclerosis affects mainly the medium-sized arteries, such as the coronary (heart) arteries, carotid (neck) arteries, cerebral (brain) arteries, and kidney arteries and is the leading cause of death and disability in the US (due to heart attacks and stroke). Atherosclerosis develops in a sequence of events. The first event is thought to be an injury that damages the inner lining of an artery. The injury may be caused by high blood pressure in the artery. Other causes may be damage by a virus, irritants such as nicotine or drugs, or an allergic reaction. White blood cells, monocytes, are then recruited into the injured wall of the artery, where they differentiate into macrophages cells and start to take up lipids. Lipids, which include fats and cholesterol, are carried all over the body by the blood. Platelets also recognize the injury and attach themselves to the injured area, they secrete growth factors which then induce muscle cell migration and proliferation. This thickens and stiffens the artery wall. The amount of fibrous, or connective, tissue in the injured area increases and forms a plaque. If a plaque becomes unstable and ruptures, a heart attach, stroke or kidney failure can result. Surgical methods to open blocked arteries include coronary artery bypass, or balloon angioplasty, in some cases to implant stents to support the artery. Restenosis, a response involving smooth muscle cell proliferation and recruitment causing reclosure of the artery, can occur following surgery.

Atrial fibrillation is a heart rhythm disturbance. It occurs when the upper chambers of the heart, atria, contract in a rapid, uncoordinated way. This loss of coordination from atrial muscle quivering affects the ability of the heart to pump blood, and increases heart rate. Common causes of atrial fibrillation are: heart disease, including coronary artery disease, heart enlargement due to many years of high blood pressure, and heart failure from other causes as well as damage to the mitral valve (located between the upper and lower left heart chambers) usually due to rheumatic fever, or mitral valve prolapse, a malfunction of the valve. The most serious complication of atrial fibrillation is a stroke caused by a blood clot in the brain.

Angina pectoris causes a feeling of tightness, squeezing, or pain in the chest, when the heart does not get enough oxygen-rich blood. Angina may be caused by any condition that affects the blood flow to the heart, such as: coronary artery disease, coronary artery spasm, abnormal heart valves, uncontrolled high blood pressure, etc. The symptoms of angina are often controlled with nitrates such as nitroglycerin that increase the blood flow to the heart, beta blockers and calcium channel blockers. Other drugs include ACE (angiotensin-converting enzyme) inhibitors, aspirin, and cholesterol-lowering medicines.

Deep vein thrombosis (DVT) occurs when a blood clot forms in a deep-lying vein, usually in the legs. Such a clot is dangerous because the clot may break loose and block arteries in your lungs, causing permanent damage or death. DVT may occur when the blood moves through deep veins in your legs more slowly than normal or when there is some factor that makes your blood more likely to clot. The risk of DVT is increased in patients with the following conditions: prolonged sitting, immobility or bedrest, orthopedic surgery, stroke, congestive heart failure, varicose veins. DVT is treated with anti-coagulants.

Heart failure is one of the most common causes of heart-related illness and death in the US. Heart failure occurs when the heart muscle fails to pump enough blood to meet the body's needs and the veins, tissues, and lungs become congested with fluid. First, pressure in the heart rises and blood and fluid back up into the lungs. Patients feel short of breath and get tired easily. If the condition worsens, the higher pressure causes a buildup of fluid in the veins and the feet, legs, and ankles will begin to swell. Heart failure may result from one or more of the following: coronary artery disease (blockage in the coronary arteries), heart attack, uncontrolled high blood pressure, a heart infection, severe lung disease or valve damage. A number of factors may worsen or trigger heart failure: severe anemia, hyper- or hypothyroidism, fever, being overweight, a high salt diet or rapid heart rate. Therapies for heart failure include: ACE inhibitors, beta blockers, digitalis, diuretics, inhibitors of aldosterone.

Arterial hypertension, or the elevation of systolic and/or diastolic BP, either primary or secondary, is frequently associated with pressure overload of the heart, and is an important risk factor for heart failure. Hypertensive patients may be analyzed by the diagnostic methods of the invention, in order to determine whether there is a concurrent development of hypertrophy, diastolic dysfunction, and a tendency to heart failure. Criteria for hypertension is typically over about 140 mm Hg systolic blood pressure, and/or diastolic blood pressure of greater than about 90 mm Hg.

Primary (essential) hypertension is of unknown etiology; its diverse hemodynamic and pathophysiologic derangements are unlikely to result from a single cause. Heredity is a predisposing factor, but the exact mechanism is unclear. The pathogenic mechanisms can lead to increased total peripheral vascular resistance by inducing vasoconstriction and to increased cardiac output. Coronary, cerebral, aortic, renal, and peripheral atherosclerosis are more common and more severe in hypertensives because hypertension accelerates atherogenesis.

The term "stroke" broadly refers to the development of deficits associated with impaired blood flow, regardless of cause. Potential causes include, but are not limited to, thrombosis, hemorrhage and embolism. Current methods for diagnosing stroke include symptom evaluation, medical history, chest X-ray, ECG (electrical heart activity), EEG (brain nerve cell activity), CAT scan to assess brain damage and MRI to obtain internal body visuals. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from a tumor, or other blood loss.

A stroke occurs when a blood vessel leading to the brain becomes blocked or bursts, damaging brain tissue. A thrombotic or embolic stroke occurs when a blood clot (thrombus) forms in an artery and blocks blood flow to the brain, or debris from a plaque breaks away and flows through the bloodstream to the brain. A cerebral hemorrhage, which is less common, occurs when an artery in the brain tears or bursts, causing blood to spill out. A number of factors increase the risk of stroke: high blood pressure, diabetes, high cholesterol, smoking, atherosclerosis or heart disease. Treatments to reduce the risk of stroke include: controlling high blood pressure and blood sugar (diabetics), controlling irregular heart rate (warfarin, aspirin or clopidogrel). Although clot lysis can be beneficial to some patients, it is not widely used.

Myocardial infarction (MI), or heart attack occurs when there is a sudden, complete blockage of blood flow to a portion of heart muscle. As coronary arteries become narrowed by the buildup of cholesterol plaque, less blood can go through them, and less oxygen gets to the heart muscle. In addition, the more likely it is that a blood clot may form and block the artery completely, causing a heart attack. A heart attack may also occur when the heart muscle needs more oxygen than the blood vessels can provide, for example during hard exercise or with a sudden increase in blood pressure. Less commonly, a heart attack can occur due to coronary spasm, a sudden and temporary narrowing of a small part of an artery that supplies blood to the heart. The lack of blood and oxygen during a heart attack damages the heart muscle. Early treatment of heart attacks is critical to try to unblock the arteries and limit the amount of muscle death. Heart attacks can cause death in several ways. If too much muscle dies, the heart is not able to pump enough blood to the rest of the body. Alternatively, targeted damage to the heart cells that regulate the heartbeat may cause fatal heart rhythm problems. And if the heart muscle weakens and is torn as a result of the damage, the resulting hemorrhage can be fatal. Treatments include medications to dissolve blood clots, lower blood pressure, reduce cholesterol and stabilize heart rhythm (e.g. beta-blocker, aspirin, etc.) In some cases, balloon angioplasty or a stent to improve blood flow to the heart is prescribed.

Diabetes is a risk factor for cardiovascular conditions. Diabetes occurs when the pancreas does not make enough insulin or is unable to use the insulin effectively. Insulin is a hormone produced by the pancreas that helps blood sugar enter cells from the blood. Normally, the body breaks down much of the food into sugar (glucose), for use by cells for energy. Thus, insulin lowers the level of sugar in the blood. When the body does not make enough insulin or has trouble using insulin, the cells do not absorb enough sugar from the blood, leading to high blood sugar levels and diabetes. Type 2 diabetes, non-insulin-dependent diabetes or adult-onset diabetes is more common than type 1 diabetes, in which the pancreas produces very little or no insulin. Complications of diabetes include eye (diabetic retinopathy), kidney (nephropathy), nerve (neuropathy), and heart and blood vessel damage and diabetics have an increased risk for heart disease, heart attacks and strokes. Controlling blood pressure and blood glucose levels, as well as cholesterol helps prevent these complications. Type 1 diabetes is treated with insulin therapy and insulin-sensitizers may be prescribed for Type 2 diabetes.

Metabolic syndrome occurs when abnormalities in glucose and lipid (blood fats) metabolism, obesity, and high blood pressure occur together. Metabolic syndrome, also known as syndrome X or insulin resistance syndrome, is defined as the presence of 3 or more of the following: obesity, low levels of HDL cholesterol, high triglyceride levels, a blood pressure of 130 over 85 or higher, and diabetes or prediabetes. increases the risk of stroke (as well as heart disease and diabetes). When insulin resistance exists, the body attempts to overcome this resistance by secreting more insulin from the pancreas. This compensatory state of hyperinsulinemia (high insulin levels in the blood) is a marker for the syndrome, and can lead to Type II diabetes. The high insulin levels resulting from insulin resistance contribute to abnormalites in blood lipids-cholesterol and triglycerides. The typical characteristics of the syndrome, degrees of glucose intolerance, abnormal cholesterol and/or triglyceride levels, high blood pressure, and upper body obesity, are all independent risk factors for cardiac disease.

Data Analysis

The data from a typical "system", as used herein, provides a single cell type or combination of cell types (where there are multiple cells present in a well) in an in vitro culture condition. Primary cells are preferred, or in the case of mast cells, cells derived from primary cells, to avoid potential artifacts introduced by cell lines. In a system, the culture conditions provide a common biologically relevant context. Each system comprises a control, e.g. the cells in the absence of the candidate biologically active agent, although usually in the presence of the factors in the biological context. The samples in a system are usually provided in triplicate, and may comprise one, two, three or more triplicate sets.

As used herein, the biological context refers to the exogenous factors added to the culture, which factors stimulate pathways in the cells. Numerous factors are known that induce pathways in responsive cells. By using a combination of factors to provoke a cellular response, one can investigate multiple individual cellular physiological pathways and simulate the physiological response to a change in environment.

Biological contexts of interest for cardiovascular disease and cardiovascular inflammation include endothelial cells, which may be provided by coronary artery, aortic, bronchial or pulmonary artery endothelial cells, or umbilical vein endothelial cells. Primary endothelial cells respond to a large variety of cellular stimuli. Endothelial cells are highly sensitive to their environment, and they contain a large number of signaling pathways. This provides an opportunity to evaluate the effect of compounds on many pathways and/or pathway interactions. Endothelial cells participate in many disease processes. In cardiovascular inflammation, they control the migration and localization of effector leukocytes and lymphocytes and regulate thrombosis and hemostasis. Among the factors useful for stimulating endothelial cells for these purposes are TNF-α; IL-1; IFNγ; thrombin; oxidized lipids; angiotensin-II; endothelin-1; aldosterone; IL-4; IL-13; TGFβ; histamine; glucose, insulin, etc., which may be used in combinations of one, two, three, four or more factors. Endothelial cells may also be used in a coculture with the cells listed below.

Muscle cells, including smooth muscle cells, may be used in a system of the invention. Muscle cell sources of interest include human umbilical vein artery smooth muscle cells, primary aortic, bronchial, coronary or pulmonary artery smooth muscle cells. Other muscle cells of interest include skeletal muscle and cardiomyocytes, for example differentiated from bone marrow mesenchymal stem cells. SMC may be cultured alone or in combination with endothelial cells or fibroblasts. Among the factors useful in this context are IFN-γ, IL-4, IL-1, TNF, thrombin, histamine, glucose, insulin, PDGF and TGF-β.

T cells may be used, including Th1 type T cells, regulatory T cells, etc. and particularly human T cells. T cell sources of interest include peripheral blood mononuclear cell preparations, which may be unselected, thereby providing a complex mixture of myeloid and lymphocytic cells, or may be selected for expression of T cell markers, such $CD4^+$, $CD3^+$, etc. Th1 cytokines are increased in patients with coronary artery disease (Fernandes et al., (2004) Cytokine 26:131-7). A chronic Th1 assay combination can be provided by a culture of HUVEC with TNF-α and/or IL-1 and IFN-γ for 24 hours.

Lymphokine-producing activated lymphocytes (CD45RO+, CD44hi, etc.) are a hallmark of chronic inflammation. Depending on the disease environment and tissue site, activated lymphocytes can differ in their expression and function of adhesion molecules and other receptors, as well as in their production of various cytokines and other factors. The ability to selectively block lymphocyte activation associated with cardiovascular inflammation without inhibiting or suppressing lymphocyte activation associated with the ability to fight infection and neoplasia is a goal of inflammatory drug therapy. Among the factors useful for stimulating T cells for these purposes are IL-2; superantigens, including SEA, SEB, TSST, etc.; anti-CD3; anti-CD28; PHA; ConA; etc.

Fibroblasts, including neonatal fibroblasts, may be used in a system of the invention. Fibroblasts may be cultured alone, or in combination with endothelial cells, and/or smooth muscle cells. Among the factors useful in this context are included TNF-α; IFNβ; IFNγ; TGFβ; IL-4; IL-13; PDGF; FGF; histamine; etc.

Monocytes, including macrophages or foam cells, may be used in a system of the invention. Monocyte sources of interest include peripheral blood mononuclear cells. Cells may be cultured alone or in combination with endothelial cells and/or smooth muscle cells. Factors useful in stimulating monocytes or macrophages include: Zymosan, toll-like receptor ligands including LPS, lipid activators, immune complexes and antiogensin-II.

Platelets may be used in a system of the invention. Platelets sources include peripheral blood, or they can be generated from in vitro culture of megakaryocytic cells. Platelets may be cultured alone or in combination with endothelial cells and/or smooth muscle cells in the presence or absence of peripheral blood mononuclear cells. Factors useful for activating platelets include ADP, thrombin, PMA, ristocetin, TRAP peptide or collagen.

Adipocytes may be used in a system of the invention. Sources of adipocytes may include preadipocytes isolated from human subcutaneous adipose tissue samples and then differentiated ex vivo. Among the factors useful with respect to adipocyte activity are TNF-α, IL-1α, IFN-γ, TGFβ, IL-11, insulin, angiotensin II, -glucagon, and glucose.

Increased numbers of mast cells are found in atherosclerotic lesions, particularly in ruptured plaques. Mast cells may be isolated from primary sources, but are preferably generated from progenitor cells in vitro. Myeloid progenitor cells useful for such purposes are well-known in the art, and include $CD34^+$ cells from bone marrow, cord blood, mobilized stem cell populations, and the like. The progenitor cells are cultured by methods known in the art, e.g. in the presence of stem cell factor (SCF) and IL-6. Factors useful in stimulating mast cells include superoxide, complement proteins (C5a, C3a), neuropeptides (Substance P, epinephrine), toll-like receptor ligands (LPS, zymosan, etc.) IgG, IgGI, L-4; IgE; A23187; Compound 48/80; Con A; NP-BSA; etc.

The present invention can be applied to the identification of compounds that inhibit or alter cardiovascular inflammatory responses. Such compounds have utility in the treatment of cardiovascular disease.

A biomap dataset comprises values obtained by measuring parameters or markers of the cells in a system. Each dataset will therefore comprise parameter output from a defined cell type(s) and biological context, and will include a system control. As described above, each sample, e.g. candidate agent, genetic construct, etc., will generally have triplicate data points; and may be multiple triplicate sets. Datasets from multiple systems may be concatenated to enhance sensitivity, as relationships in pathways are strongly context-dependent. It is found that concatenating multiple datasets by simultaneous analysis of 2, 3, 4 or more systems will provide for enhance sensitivity of the analysis.

By referring to a biomap is intended that the dataset will comprise values of the levels of at least two sets of parameters, preferably at least three parameters, more preferably 4 parameters, and may comprise five, six or more parameters.

In many cases the literature has sufficient information to establish the system conditions to provide a useful biomap. Where the information is not available, by using the procedures described in the literature for identifying markers for diseases, using subtraction libraries, microarrays for RNA transcription comparisons, proteomic or immunologic comparisons, between normal and cells in the physiologic state of interest, using knock-out and knock-in animal models, using model animals that simulate the physiological state, by introducing cells or tissue from one species into a different species that can accept the foreign cells or tissue, e.g. immunocompromised host, one can ascertain the endogenous factors associated with the physiologic state and the markers that are produced by the cells associated with the physiologic state.

The parameters may be optimized by obtaining a system dataset, and using pattern recognition algorithms and statistical analyses to compare and contrast different parameter sets. Parameters are selected that provide a dataset that discriminates between changes in the environment of the cell culture known to have different modes of action, i.e. the biomap is similar for agents with a common mode of action, and different for agents with a different mode of action. The optimization process allows the identification and selection of a minimal set of parameters, each of which provides a robust readout, and that together provide a biomap that enables discrimination of different modes of action of stimuli or agents. The iterative process focuses on optimizing the assay combinations and readout parameters to maximize efficiency and the number of signaling pathways and/or functionally different cell states produced in the assay configurations that can be identified and distinguished, while at the same time minimizing the number of parameters or assay combinations required for such discrimination. Optimal parameters are robust and reproducible and selected by their regulation by individual factors and combinations of factors.

Parameters are quantifiable components of cells. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc.

Markers are selected to serve as parameters based on the following criteria, where any parameter need not have all of the criteria: the parameter is modulated in the physiological condition that one is simulating with the assay combination; the parameter has a robust response that can be easily detected and differentiated; the parameter is not co-regulated with another parameter, so as to be redundant in the information provided; and in some instances, changes in the parameter are indicative of toxicity leading to cell death. The set of parameters selected is sufficiently large to allow distinction between datasets, while sufficiently selective to fulfill computational requirements.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide, e.g. a phosphorylated protein, such as a STAT transcriptional protein; or sulfated oligosaccharide, or such as the carbohydrate structure Sialyl Lewis x, a selectin ligand. The presence of the active conformation of a receptor may comprise one parameter while an inactive conformation of a receptor may comprise another, e.g. the active and inactive forms of heterodimeric integrin $\alpha_M\beta_2$ or Mac-1.

Parameters of interest for the evaluation of cardiovascular inflammation include, without limitation, MCP-1, Collagen I, VCAM-1, CD40, IP-10, MIG, M-CSF, PAI-1, ICAM-1, CD90, IL-8, Eotaxin-3, Collagen III, CD36, CD163, Mac-1, endothelin-1, E-selectin, Thrombomodulin, Tissue Factor, uPAR, HLA-DR, MIP-1alpha, MIP-3alpha, MDC, MMP-13, transferrin, LDL-R, M-CSF, CD38, CD69, CD25, IFN-g, IL-1, IL-6, histamine, TNF-a, leptin, CRP, GLT4, resistin, TNFRI, TNFRII, creatine kinase, serum amyloid A, LOX-1, adiponectin, glucose, resistin, pentraxin-3, tryptase, VEGF, PDGF, TGFβR. Hepatocyte GF, P-selectin, vWF, fibrinogen, HDL, LDL, apolipoproteins, IL-11, IL-23, TGFb, MMP-1, MMP-2, MMP-9, MMP-11, TIMP-1, TIMP-2, IGF-1, EGF, VEGFR2, tPA, uPA, ITAC, C5a, C3a, PGI2, TXA2, ACE, AT2R1, angiotensin II, ANP, and nitric oxide.

Candidate biologically active agents may encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetic agents, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Compounds of interest for screening may include known anti-inflammatory drugs, analogs and derivatives thereof, or other modulators of inflammation. Such compounds may include, without limitation: histamine agonists, e.g. histamine, betazole, impromidine; histamine antagonists including H1 selective, H2 selective and non-selective blockers, e.g. doxylamine clemastine, brompheniramine triprolidine, cimetidine, chlorpheniramine, famotidine, diphenhydramine, nizatidine, promethazine, ranitidine, loratidine, levocobastine, cetirizine, acravastine; inhibitors of histamine release, e.g. cromalyn, nedocromil, eicosanoids. Leukotriene antagonists may include zafirlakast; inhibitors of leukotriene synthesis may include zileuton, montelekast, carboprost, dinoprotone, alprostadil, dinoprost, and misoprostol. Kinin modulators include bradykinin and aprotinin. NSAIDs, acetaminophen, aspirin and related salicylates are all of interest. Such drugs may include, without limitation, aspirin and salicylates, meclofenamate, celecoxib, diclofenac sodium, naproxen, rofecoxib, fenoprofen, phenylbutazone, meloxicam, ibuprofen, piroxicam, namebutone, indomethacin, sulindac, ketoprofen, and tometin. Immunosuppressants and anti-proliferatives include rapamycin, methotrexate, azathioprine, cyclosporin, FK-506, cdk inhibitors, and corticosteroids. Statins refer to a known class of HMG-CoA reductase inhibitors. These agents include mevastatin and related compounds, lovastatin (mevinolin) and related compounds, pravastatin and related compounds, simvastatin and related compounds; fluvastatin and related compounds; atorvastatin and related compounds; cerivastatin and related compounds and rosuvastatin. Other compounds of interest include cardiovascular drugs, beta blockers calcium channel antagonists, angiotensin converting enzyme inhibitors, angiotensin receptor inhibitors, and other hypertensives, alpha blockers, lipid-lowering drugs, PPAR agonists, antagonists, endothelin receptor antagonists, adenosine receptor antagonists, and diuretics.

The term "genetic agent" refers to polynucleotides and analogs thereof, which agents are tested in the screening assays of the invention by addition of the genetic agent to a cell. Genetic agents may be used as a factor, e.g. where the agent provides for expression of a factor. Genetic agents may also be screened, in a manner analogous to chemical agents. The introduction of the genetic agent results in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Agents are screened for biological activity by adding the agent to cells in the system; and may be added to cells in multiple systems. The change in parameter readout in response to the agent is measured to provide the biomap dataset.

The data, particularly data from multiple cardiovascular-disease relevant systems, may be subjected to non-supervised hierarchical clustering to reveal relationships among profiles. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions. Application of MDS produces a unique ordering for the agents, based on the distance of the agent profiles on a line. To allow objective evaluation of the significance of all relationships between compound activities, profile data from all multiple systems may be concatenated; and the multi-system data compared to each other by pairwise Pearson correlation. The relationships implied by these correlations may then be visualized by using multidimensional scaling to represent them in two or three dimensions.

Biological datasets are analyzed to determine statistically significant matches between datasets, usually between test datasets and control, or profile datasets. Comparisons may be made between two or more datasets, where a typical dataset comprises readouts from multiple cellular parameters resulting from exposure of cells to biological factors in the absence or presence of a candidate agent, where the agent may be a genetic agent, e.g. expressed coding sequence; or a chemical agent, e.g. drug candidate.

A prediction envelope is generated from the repeats of the control profiles; which prediction envelope provides upper and lower limits for experimental variation in parameter values. The prediction envelope(s) may be stored in a computer database for retrieval by a user, e.g. in a comparison with a test dataset.

In one embodiment of the invention, the analysis methods provided herein are used in the determination of functional homology between two agents. As used herein, the term "functional homology" refers to determination of a similarity of function between two candidate agents, e.g. where the agents act on the same target protein, or affect the same pathway. Functional homology may also distinguish compounds by the effect on secondary pathways, i.e. side effects. In this manner, compounds or genes that are structurally dissimilar may be related with respect to their physiological function. Parallel analyses allow identification of compounds with statistically similar functions across systems tested, demonstrating related pathway or molecular targets. Multi-system analysis can also reveal similarity of functional responses induced by mechanistically distinct drugs.

Classes of agents acting in cardiovascular disease-associated contexts include cholesterol or lipid lowering drugs, beta-blockers, ACE inhibitors, calcium channel blockers, other anti-hypertensive agents, diuretics, anti-platelet drugs including aspirin, insulin sensitizers, anti-coagulants, and thrombolytic agents. Compounds in these classes may be used to generate known profiles for activity. Additionally, compounds in these classes may be tested for therapeutic profiles in the assays of the present invention, e.g. where derivatives and analogs of known agents are tested for activity; agents sharing common structural features with known agents in these classes, and the like.

EXAMPLES

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is particularly to be understood that the present invention is not limited to the particular embodiments described herein. For example, the invention is not restricted to the particular methodology, protocols, cell lines, animal species or genera, constructs and reagents described herein as such may vary. The foregoing has been merely a description of certain preferred embodiments of the invention, not intended to limit the scope of that invention, which is defined only by the appended claims.

Example 1

Multisystem Analysis of CV Drugs 3C, 4H, LPS, SAg

The present invention is applied for the screening of compounds for cardiovascular disease.

Compounds are screening by testing in the following BioMAP model systems:

| System | Cell Types | Environment | Readout Parameters |
| --- | --- | --- | --- |
| 3C | Primary Human Endothelial Cells | IL-1β + TNF-α + IFN-γ | E-selectin, VCAM, ICAM, MCP-1, MIG, IL-8, HLA-DR, uPAR, TF |
| 4H | Primary Human Endothelial Cells | IL-4 + histamine | VEGFRII, P-selectin, VCAM, uPAR, Eotaxin-3, MCP-1 |
| LPS | Peripheral Blood Mononuclear Cells + Endothelial Cells | TLR4 | CD14, TF, TM, CD40, CD69, MCP-1, E-selectin, IL-1α, IL-8, M-CSF, VCAM |
| SAg | Peripheral Blood Mononuclear Cells + Endothelial Cells | TCR | CD38, CD40, CD69, E-selectin, IL-8, MCP-1, MIG |

Human umbilical vein endothelial cells (HUVEC) were cultured according to standard methods, and plated into microtiter plates. Peripheral blood mononuclear cells (PBMC) were prepared from buffy coats from normal human donors according to standard methods. Experiments were performed by culturing HUVEC in microtiter plates in the presence of cytokines (IL-1b, 1 ng/ml; TNF-a, 5 ng/ml; and IFN-g, 100 ng/ml, or IL-4, 5 ng/ml and histamine, 10 mM), activators (SAg, 20 ng/ml or LPS, 0.2 ng/ml), and/or PBMC ($7.5 \times 10^4$ cells/well) for 24 h. Compounds were tested at the indicated concentrations. Compounds were prepared in the solvent as directed, added 1 hr before stimulation of the cells, and were present during the whole 24 hr stimulation period.

The levels of readout parameters (proteins) were measured by cell-based ELISA. Briefly, microtiter plates are treated, blocked, and then incubated with primary antibodies or isotype control antibodies (0.01-0.5 mg/ml) for 1 hr. After washing, plates were incubated with a peroxidase-conjugated anti-mouse IgG secondary antibody or a biotin-conjugated anti-mouse IgG antibody for 1 hr followed by streptavidin-HRP for 30 min. Plates were washed and developed with TMB substrate and the absorbance (OD) was read at 450 nm (subtracting the background absorbance at 650 nm). Other readout parameters include: total protein levels (SRB assay), measuring the viability of peripheral blood mononuclear cells (incorporation of propidium iodide); and microscopic visualization. SRB was performed by staining cells with 0.1% sulforhodamine B after fixation with 10% TCA, and reading wells at 560 nm. PBMC viability was assessed by adding propidium iodide (10 mg/ml) to PBMC that had been cultured for 24 hours in the presence of activators and measuring the percentage of cells that incorporated dye by flow cytometry after 10 minutes.

For data analysis, mean OD values (or other measurements) for each parameter were calculated from triplicate samples per experiment. The mean value obtained for each parameter in a treated sample was then divided by the mean value from an appropriate control to generate a ratio. All ratios were then log 10 transformed. An average or "trusted" profile was created by averaging 2 repeats of the experiment for each compound and concentration combination. 99% prediction envelopes (grey shading in Figures) were calculated for historical controls. FIG. 1 shows the 4 system BioMAP activity profile for lovastatin, an HMG-CoA reductase inhibitor.

Key features of the lovastatin profile are significant decreases in uPAR, MCP-1, IL-1 alpha and CD69 in the 3C, 4H, LPS and SAg systems, respectively, and increases in Eotaxin-3 and P-selectin in the 4H system, tissue factor and M-CSF in the LPS system and E-selectin and IL-8 in the SAg system. Many statins, including atorvastatin, mevastatin, simvastatin and cerevistatin induce the same BioMAP profile (not shown). In addition, many features, including the effects on MCP-1, Eotaxin-3, P-selectin, IL-a, E-selectin CD69 and IL-8 are also induced by inhibitors of geranylgeranyltransferase (GGTIs). This enzyme acts at a step downstream of HMG-CoA reductase and geranlylates certain proteins including GTPases, such as rac and RhoA. Geranlygeranyltransferase is not in the pathway of cholesterol synthesis, suggesting that many activities of statins are independent of cholesterol synthesis. Other lovastatin profile features, such as the increase in tissue factor in the LPS system, is also seen with inhibitors of farnesyltransferase (FTIs), another enzyme downstream of HMG-CoA reductase that mediates protein farnesylation. This enzyme is also not in the cholesterol synthesis pathway.

Comparison of the lovastatin BioMAP profile to a database of compound profiles allows mechanistic interpretation of the activities. The downregulation of MCP-1 in the 4H system suggests an effect on NADPH oxidase. The ability of GGTIs to also downregulate MCP-1 in this system, suggests that this effect is due to statin inhibition of a geranlylated protein. The rac GTPase is a geranlylated protein that regulates NADPH oxidase. NADPH oxidase associates with the IL-4 receptor and produces superoxide and ROS. Since MCP-1 is induced by superoxide and ROS, this suggests that statins block MCP-1 production in this system by inhibiting rac-dependent NADPH oxidase.

Tissue factor is a protein involved in hemostasis, coagulation and angiogenesis. In the LPS system, tissue factor expression is upregulated by statins as well as by inhibitors of PI-3 kinase and AKT. Inhibitors of NFkappaB, p38 and MEK kinase block the expression of tissue factor in this system. Tissue factor is not upregulated by GGTIs, suggesting this activity depends on farnesylation or cholesterol directly. AKT activation has been shown to be dependent on cholesterol content in lipid rafts.

The inhibition of CD69 in the SAg system by statins is also a feature of TGFbetaReceptor kinase inhibitors. In contrast, inhibitors of PI-3 kinase, and rapamycin (an inhibitor of FKBP12/mTOR) upregulate CD69. CD69 has been shown to induce TGFbeta production (Sancho, 2003, J. Clin. Invest. 112:872), and FKBP12 has been shown to block TGFbeta signaling (Chen, 1997, Embo J. 16:3866). TGFbeta signaling is involved in cardiovascular disease. TGFbeta has been shown to promote myocardial fibrosis, and is increased in cardiac hypertrophy and correlates to progression to heart failure Lijnen, 200, Mol. Genet. Metab. 71:418; Hein, 2003, Circ. 107:984). Inhibition of TGFbeta also reduces intimal lesion formation in carotid balloon injury models and prevents late remodeling after infarction (Ikeuchi, 2004, Cardiovas. Res. 64:526; Smith, 1999 Cir. Res. 84:1212). Statin inhibition of TGFbeta signaling activities may be related to clinical activity.

In the SAg system, the upregulation of E-selectin and IL-8, with downregulation of CD69 is an unusual set of features. This feature is shared by inhibitors of PI-PLC (ET-18-OCH3; Powis, 1992, Cancer Res. 52:2835) and PC-PLC (D609; Singh, 200, Biochim. Biophys Acta 1487: 201). Phospholipases (PLCs) generate diacylglycerol (DAG) from membrane lipids. Inhibitors of PLC limit the production of DAG and subsequent signaling pathways activated by DAG (PKC, PLA2, etc.). DAG is metabolized to phosphatidic acid by DAG kinase. DAG kinase is negatively regulated by RhoA, thus, statin inhibition of RhoA (a geraylated small GTPase), could also limit the production of DAG by increasing activity of DAG kinase. Reduction of DAG mediated signaling, and increase in phosphtidic acid signaling (e.g. IL-2 signaling) may modulate a number of cell processes, including T cell responses to IL-2, potentially altering the differentiation of Th2 cells which is dependent on high concentrations of IL-2. The increase in Eotaxin-3 and P-selectin in the 4H system, both of which are dependent on IL-4 signaling also supports a role for Th2/Th1 modulation by statins.

The inhibition of IL-1 alpha in the LPS system (without concomitant decreases in E-selectin or tissue factor), and the increase in Eotaxin-3 and P-selectin in the 4H system are unusual features. Opposite effects (increase in IL-1alpha and decrease in Eotaxin-3 and P-selectin) are observed with compounds that induce mitochondrial uncoupling or permeability transition. This include inhibitors of the F0F1-ATPase, and modulators of adenine nucleoside translocator (ANT) or VDAC. Mitochondrial uncoupling occurs when protons generated by oxidative phosphorylation by the electron transport chain, are not efficiently converted to ATP, but are dissipated as heat (proton leak). The reverse activities of statins suggest that statins may have an opposite effect—that of tightening the coupling of mitochondrial oxidative phosphorylation to ATP synthesis, thereby increasing the efficiency of ATP synthesis. This feature may be related to the beneficial effects of statins in heart failure. Less efficient ATP synthesis may contribute to heart failure (Murray, 2004, Lancet 364:1786) and permeability transition pore has been shown to contribute to myocardial disease (Weiss, 2003, Circ Res. 93:292).

FIG. 2 shows a Function Homology Map of various compounds relevant to cardiovascular disease and the ability of the 4 BioMAP models described above to classify them by mechanism/target. Compounds and concentrations in FIG. 2 are shown in the table below:

| Mechanism/Target | Compound, Concentration in nM |
|---|---|
| Angiotensin Converting Enzyme | Captopril, 100000.0 nM |
| Angiotensin Converting Enzyme | Enalaprilat, 100000.0 nM |
| Angiotensin Converting Enzyme | Lisinopril, 50000.0 nM |
| Beta Adrenergic Receptor | ICI-118551, 50000.0 nM |
| Beta Adrenergic Receptor | Propranolol, 33333.333 nM |
| Beta Adrenergic Receptor | S-propranolol, 50000.0 nM |
| Calcineurin | Cyclosporin A, 3333.333 nM |
| Calcineurin | FK-506, 3333.333 nM |
| cGMP agonist | 8-pCPT-cGMP, 200000.0 nM |
| Corticosteroid | Budesonide, 10000.0 nM |
| Corticosteroid | Dexamethasone, 10000.0 nM |
| Corticosteroid | Prednisolone, 10000.0 nM |
| Cyclin D kinase | GW8510, 2777.778 nM |
| Cyclin D kinase | Kenpaullone, 10000.0 nM |
| Cyclin D kinase | Olomoucine, 33333.333 nM |
| Cyclin D kinase | Roscovitine, 8333.333 nM |
| FKBP12/mTOR | Rapamycin, 333.333 nM |
| Histamine H1 receptor | Astemizole, 617.284 nM |
| Histamine H1 receptor | Clemastine, 2777.778 nM |
| Histamine H1 receptor | Ketotifen Fumarate, 8333.333 nM |
| Histamine H1 receptor | trans-Triprolidine, 22222.222 nM |
| HMG-CoA reductase | Atorvastatin, 1111.111 nM |
| HMG-CoA reductase | Lovastatin, 3333.333 nM |
| HMG-CoA reductase | Mevastatin, 370.37 nM |
| HMG-CoA reductase | Simvastatin, 3333.333 nM |
| Hsp90 | 17-AAG, 3333.333 nM |
| Hsp90 | Geldanamycin, 3333.333 nM |
| Hsp90 | Radicicol, 3333.333 nM |
| Immunosuppressive (DOODH) | Leflunomide, 66666.667 nM |
| Immunosuppressive (rac GTPase) | Azathioprine, 50000.0 nM |
| MEK kinase | PD098059, 10000.0 nM |
| MEK kinase | SL327, 10000.0 nM |
| MEK kinase | UO126, 10000.0 nM |
| MEK kinase | UO126, 3333.333 nM |
| MEK kinase | UO126, 1111.111 nM |
| MEK kinase | UO126, 370.37 nM |
| NSAID | Ibuprofen, 666666.667 nM |
| NSAID | Indomethacin, 50000.0 nM |
| p38 kinase | PD169316, 1111.111 nM |
| p38 kinase | SB220025, 3333.333 nM |
| p38 kinase | SB239063, 3333.333 nM |
| p38 kinase (JNK) | SB202190, 1851.852 nM |
| p38 kinase (JNK) | SB203580, 1851.852 nM |
| PI-3 kinase | LY294002, 3333.333 nM |
| PI-3 kinase | Wortmannin, 3333.333 nM |
| PPARgamma | Troglitazone, 8333.333 nM |
| Src family kinase (lck) | PP1, 5000.0 nM |
| Src family kinase (lck) | PP2, 5000.0 nM |

Example 2

Regulators of Aortic Endothelial Cell Responses

The present invention is applied for the screening of compounds that modulate aortic endothelial responses.

Primary human coronary artery endothelial cells are used. Other cells that may replace HCAEC in the screen include: primary aortic, bronchial, coronary artery or pulmonary artery smooth muscle cells. Passage 5 to 7 cells are used for the screen. $7.5 \times 10^4$ cells/ml are cultured to 100% confluence in EGM-2MV media.

One or more of the following are then applied for 24 hours: PAPC 15 ug/ml, PGPC 15 ug/ml, oxLDL 50 ug/ml, angiotensin-II 10 uM, thrombin, as well as cytokines IL-1b, 1 ng/ml; TNF-a, 5 ng/ml; and IFN-g, 100 ng/ml, or IL-4, 5 ng/ml and histamine, 10 mM, TGF-beta 10 ng/ml, endothelin-1 200 nM, aldosterone (1 uM), and activators LPS 0.2 ng/ml, Poly(I:C), 1 µg/ml.

Based on the parameters altered by the indicated factors, BioMAPs are generated for the parameters VCAM, CD40, HLA-DR, ICAM, IL-8, MCP-1, M-CSF, MIG, Thrombomodulin, tissue factor, VEGFRII and CD69 (AIM). Other markers of interest include: ACE, alpha5beta1, IP-10, alpha-smooth muscle actin, Collagen I, FGF receptor, IL-6, LDL receptor, MMP1, MMP2, PAI-1 and VEGF receptor II, E-selectin, P-selectin, angiotensin converting enzyme (ACE), urokinase-type plasminogen activator receptor (uPAR), PAI-1, tissue factor pathway inhibitor (TFPI), tPA, thrombospondin, and IL-6 (Devaux, Eur. Heart J. 18:470, 1997; Kessler, Diabetes Metab. 24:327, 1998; Becker, Z. Kardiol. 89:160, 2000; Kaplanski, J. Immunol. 158:5435, 1997; Li, Circulation 102:1970, 2000). Other markers of interest for adding to the BioMAP include vWF, fibrinogen-binding activity, angiotensin-1 receptor, endothelin-1 receptor and CD36 (Paramo, Br. Med. J. 291:573, 1985; Fukuhara, Hypertension 35:353, 26000; Noda-Heiny, Arterioscler Thromb Vasc. Biol. 15:37, 1995; de Prost, J. Cardiovasc. Pharmacol., 25 Suppl2:S114, 1995; van de Stolpe, Thromb Haemost 75:182, 1996; Mach, J. Clin. Invest., 104:1041, 1999; Nicholson, Ann. N.Y. Acad. Sci., 902:128, 2000). Other factors of interest include adiponectin and resistin.

Example 3

Regulators of Muscle Cell Responses SM3C, SMThr

The present invention is applied for the screening of compounds that modulate smooth muscle cell, skeletal muscle cell or cardiomyocyte responses.

Primary human umbilical artery smooth muscle cells (UASMC) are used. Other cells that may replace UASMC in the screen include primary aortic, bronchial, coronary artery or pulmonary artery smooth muscle cells. Other muscle cells of interest include skeletal muscle cells and cardiomyocytes. Passage 5-7 cells are used for the screen. $4 \times 10^4$ cells/ml are cultured to 100% confluence on CellBind plates (Costar) in SmGM-2 (Clonetics) containing 5% FBS. In some cases, SmGM-2 may be removed 24 hours before screen, and replaced with serum-free SmBM basal media (Clonetics) supplemented with insulin.

The following are then applied for 24 hours: Factors include a combination of IL-4 (5 ng/ml), and histamine (HIS) (10 µM) or a combination of IL-1 (1 ng/ml), TNF-a (5 ng/ml) and IFNg (20 ng/ml) (SM3C) and/or thrombin (10 units/ml) for 6 and/or 24 hours. Standard concentrations of agents are employed as described in the literature. Other factors of interest include: IL-6, LPS, endothelin-1 and angiotensin II.

Based on the parameters altered by the indicated factors, BioMAPs are generated for the parameters VCAM, HLA-DR, IL-8, MCP-1, Thrombomodulin, tissue factor, LDL-receptor and uPAR. Other markers of interest include: ACE (CD143), adiponectin, alpha5beta1, creatine kinase, ICAM-1, IP-10, alpha-smooth muscle actin, cardiac alpha-actin, skeletal alpha-actin, CD40, Collagen I, FGF receptor, IL-1, IL-6, IGF-1, M-CSF, MIF (MRP-8), MIG, MMP1, MMP2, MMP9, TGFbeta, TNFalpha, PDGFBB, serum amyloid A, angiotensin II receptor-1, myosin light chain kinase, myosin heavy chain 1, myosin heavy chain 2, thrombospondin-1, PAI-1 and VEGF receptor II.

FIG. 3 shows the BioMAP profile of atorvastatin, an HMG-CoA reductase inhibitor, in the SM3C system.

Example 4

Regulators of Fibroblast Responses HDF-3C/TGF, HDF-TGF, HDF-IL4/IL13/TNF, HDF-IL4/IL13/GF The present invention is applied for the screening of compounds that inhibit fibroblast responses.

Human neonatal fibroblasts (HDFn) are used. Cells are cultured at $4 \times 10^4$ cells/ml in DMEM/F12 (50/50) from Celigro, supplemented with LSGS kit (from Cascade Biologics); fetal bovine serum, 2% v/v, hydrocortisone 1 ug/ml, human epidermal growth factor (hEGF) 10 ng/ml, basic fibroblast growth factor 3 ng/ml and heparin 10 ug/ml, and penicillin/streptomycin amphotericin B solution (PSA), until confluency. Medium is replaced with DMEM/F12 with only penicillin/streptomycin amphotericin B solution (PSA), then 24 hours prior stimulation, then the following are applied: TNF (5 ng/ml), IFN (20 ng/ml) and TGFb (20 ng/ml) or TGFb (20 ng/ml), or TGFb (20 ng/ml) with 5 ng/ml IL-4 and/or IL-13. Growth factors such as FGF, PDGF, IGF, or EGF can be added alone or in combination to any of the previous stimulations as well. Other factors of interest include Angiotensin-II.

After another 24 hours incubation (37° C., 5% $CO_2$) the cultures are evaluated for the following parameters: for the HDF3CT system: ICAM, VCAM, CD40, IP-10, MCP-1, Collagen I, Mig M-CSF, PAI-I, IL-8; for the HDFT system: Collagen 1, HLA-DR, PAI-I, TIMP-2. Other parameters of interest include endothelin-1, IL-6, collagen III, PDGFR, TIMP-1, MMP-1, MMP-9, MMP-2, uPA, GM-CSF, and alpha smooth muscle actin, TGFbeta.

A database of biomaps is generated from a panel of assay combinations that include the presence and absence of each biologically active factor; and anti-inflammatory drug compounds including inhibitors of fibroblast activation and/or proliferation including metabolic enzyme inhibitors, signaling inhibitors; as well as immune stimulatory agents including pathogens or pathogen components, etc. are screened and biomaps generated that show the changes in the markers with the different agents. Such compounds are given in The Pharmacologic Basis of Therapeutics. The biomaps with the known agents are used to compare to candidate agents. This allows the recognition of the pathway(s) the candidate agent acts on, by comparing the changes in the level of the specific markers for known drugs affecting known pathways and the changes observed with the candidate agent. In addition to further add to the utility of the biomap, one may include in the database reference biomaps generated from assay panels containing cells with genetic constructs that selectively target or modulate specific cellular pathways (e.g., NFkB, MAP kinase, etc), or cells that contain known genetic mutations.

Example 5

Regulators of Macrophage Responses

The present invention is applied for the screening of compounds that inhibit the macrophage cell responses.

Macrophages, are generated from human peripheral blood mononuclear cells. Human peripheral blood mononuclear cells are isolated from blood by Ficoll-hypaque density gradient centrifugation as described (Ponath, JEM 183: 2437, 1996). Monocytes are then isolated by negative selection using the Monocyte Isolation Kit II (Miltenyi Biotec, Germany) MACS beads according to the manufacturer's instructions. Alternatively, $10 \times 10^6$ peripheral blood mononuclear cells/ml are cultured in RPMI containing 10% fetal bovine serum for 3 hours and non-adherent lymphocytes are removed by gentle washing. The following are then applied for 7 to 8 days: MCSF (50 ng/ml) alone, or MCSF+one of the following cytokines, IL-4 (20 ng/ml), IL-6 (20 ng/ml), IFN-gamma (10 ng/ml), or GM-CSF (10 ng/ml)+IL-4 (20 ng/ml). To generate foam cells, the culture media is replaced with media containing 40% autologous serum or 40% Human AB Serum male (Cambrex Bioproducts) in RPMI+ MCSF 50 ng/ml for an additional 4 to 5 days. Cells are harvested and resuspended to $10^6$ cells/ml and added to confluent endothelial cells.

Primary human umbilical vein endothelial cells (HUVEC) are used. Other cells that may replace HUVEC in the screen include primary microvascular endothelial cells, aortic or arteriolar endothelial cells. $7.5 \times 10^4$ cells/ml are cultured to confluence in EGM-2 (Clonetics). Other media that may replace EGM-2 include EGM or EGM-2MV (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984).

Following addition of macrophages to endothelial cells, the following are applied: test agent or buffer control and Zymosan (10 μg/ml) (Mphg system), cell wall preparation from *Saccharomyces cerevisiae* (Underhill D M, et al., Nature, 401(6755):811-5, 1999). Other stimulants that can be substituted for Zymosan in this system include Toll-like receptor ligands such as Poly(I:C) dsRNA, oligonucleotides with human CpGs, Loxoribine, Pam3Cys synthetic lipoprotein, peptidoglycans, LPS, lipid activators such as PAPC 15 ug/ml, PGPC 15 ug/ml, oxLDL 50 ug/ml, angiotensin-II 10 uM, or immune complexes such as heat agglutinated IgG, anti IgG/IgG, and IgG coated onto microspheres (Polysciences, Inc.).

Based on the parameters altered by the indicated factors, biomaps are generated for the parameters CD40, CD69, E-Selectin, IL-1alpha, IL-8, M-CSF, MIP-1a, MCP-1, MIG, urokinase-type plasminogen activator receptor (uPAR, CD87), tissue factor (CD142), thrombomodulin and VCAM-1 (CD106). Other parameters of interest include CD4, CD14, CD86, TNF-alpha, IL-1beta, IL-6, IL-10, IL-12, IL-18, PLA2, MIP-3alpha, CD163, CD36, Mac-1 (CD11b/CD18), MDC, MMP9, MMP13, and transferrin.

The BioMAP profile for atorvastatin in the Mphg system is shown in FIG. 4.

Example 6

Regulators of Platelet Functions Plt_EC, Plt_SMC

The present invention is applied for the screening of compounds that modulate platelet/endothelial, and platelet/smooth muscle cell responses.

Primary human umbilical artery smooth muscle cells (UASMC) are used. Other cells that may replace UASMC in the screen include primary aortic, bronchial, coronary artery or pulmonary artery smooth muscle cells; cardiomyocytes or skeletal muscle cells. Passage 5-7 cells are used for the screen. $4 \times 10^4$ cells/ml are cultured to 100% confluence on CellBind plates (Costar) in SmGM-2 (Clonetics) containing 5% FBS. In some cases, SmGM-2 may be removed 24 hours before screen, and replaced with serum-free SmBM basal media (Clonetics) supplemented with insulin. Primary human umbilical vein endothelial cells (HUVEC) are also used. Other cells that may replace HUVEC in the screen include primary microvascular endothelial cells, aortic or arteriolar endothelial cells. $7.5 \times 10^4$ cells/ml are cultured to confluence in EGM-2 (Clonetics). Other media that may replace EGM-2 include EGM or EGM-2MV (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984).

Human platelets are isolated from acid citrate dextrose solution (A)-anti-coagulated whole blood. Platelet-rich plasma (PRP) is obtained by centrifugation at 1600 rpm for 10 minutes. Platelets are pelleted by centrifugation of PRP at 3000 rpm for 20 minutes. Platelets are washed in divalent cation-free Tyrode's buffer (0.1% BSA, 5.5 mM glucose, 2.7 mM Kcl, 12 mM $NaHCO_3$, 135 mM NaCl, 10 mM HEPES, pH 7.2). Platelet activation during isolation may be prevented by addition of 10 nM PGE, 1 mM theophylline, and or 1 unit/ml apyrase. Platelets in PRP or platelets resuspended in Tyrode's buffer containing 1 mM CaCl2 and 2 mM MgCl2 to a concentration of $2 \times 108$/ml can be used for assays. Factors are applied for 10 minutes with gentle shaking and include ADP (20 microM), thrombin (0.2 units/ml), epinephrine (10 microM), PMA (150 nM), ristocetin (1 mg/ml), collagen (1 microg/ml) or TRAP (10 microM). Activated or resting platelets are then incubated (0.5-108/ml) with HUVEC or SMC which have been cultured as described above, for 6-24 hours.

Based on the parameters altered by the indicated factors, biomaps are generated for the parameters MCP-1, ICAM-1, gpIIb/IIIa, P-selectin, tissue factor, VCAM-1, vWF, uPAR, thrombomodulin, MMP-1, MMP-2 and MMP-9, uPA, tPA, CD40, CD40L, E-selectin, PDGF.

Example 7

Regulators of Muscle Cell/EC Responses SMC_EC

The present invention is applied for the screening of compounds that modulate muscle cell/endothelial cell responses.

Primary human umbilical artery smooth muscle cells (UASMC) are used. Other cells that may replace UASMC in the screen include primary aortic, bronchial, coronary artery or pulmonary artery smooth muscle cells; cardiomyocytes or skeletal muscle cells. Passage 5-7 cells are used for the screen. Human umbilical vein endothelial cells, passage 3-4, are cultured with the SMC at a ratio of 7500 HUVEC to 2500 SMC, per 0.1 ml and allowed to grow together to confluency in 50/50 SMGM2/EGM-2 media (Clonetics). In some cases, media may be removed 24 hours before screen, and replaced with serum-free SmBM basal media (Clonetics) supplemented with insulin.

The following are then applied for 24 hours: Factors include a combination of IL-4 (5 ng/ml), and histamine (HIS) (10 μM) or a combination of IL-1 (1 ng/ml), TNF-a (5 ng/ml) and IFNg (20 ng/ml), and or thrombin (10 units/ml) for 6 and/or 24 hours. Standard concentrations of agents are employed as described in the literature. Other factors of interest include IL-6, TLR2 and TLR4 activators (LPS, zymosan, bacterial peptidoglycan), endothelin-1, angiotensin II.

Based on the parameters altered by the indicated factors, BioMAPs are generated for the parameters VCAM, CD40, HLA-DR, ICAM, IL-8, MCP-1, M-CSF, MIG, Thrombomodulin, tissue factor and uPAR. Other markers of interest include: P-selectin, E-selectin, Eotaxin-3, ACE, adiponectin, alpha5beta1, IP-10, alpha-smooth muscle actin, cardiac alpha-actin, skeletal alpha-actin, Collagen I, creatine kinase, FGF receptor, IGF-1, IL-1, IL-6, LDL receptor, MIF, MMP1, MMP2, MMP9, TGFbeta, PDGFBB, serum amyloid A, angiotensin II receptor-1, myosin light chain kinase, myosin heavy chain 1, myosin heavy chain 2, TNF-a, thrombospondin-1, PAI-1 and VEGF receptor 11.

Example 8

Regulators of Mast Cell Responses EC_Mast, SMC_Mast, EC_SMC_Mast

The present invention is applied for the screening of compounds that inhibit the mast cell responses.

Mast cells generated from CD34$^+$ Umbilical Cord Blood are used. Cryopreserved CD34$^+$ Umbilical Cord Blood (UCB) cells are obtained from AllCells, LLC or Cambrex. CD34$^+$ UCB cells can also be isolated from unfractionated UCB using Miltenyi CD34-isolation kits. CD34$^+$ UCB cells are cultured with 100 ng/ml SCF and 50 ng/ml IL-6 (Peprotech) in Yssel's Media (Gemini) or IMDM (Mediatech) supplemented with 2% FBS or 2% BSA (Sigma) and 1× Pen/Strep (Mediatech), 5 mM 2-ME (Gibco), 1× Insulin/Trasferrin/Selenium A (Gibco), 1 mM Na Pyruvate (Gibco) and 0.1 mM MEM Non-essential Amino Acids (Gibco) or IMDM with 10% FBS. Other supplements for derivation of mast cells may include IL-9, IL-10, TPO, FLT-3L, PGE-2, IL-3 and human IgE. Cells are cultured in 6-well plates. Every 7 days, one half of the media is replaced with fresh media supplemented with IL6 and SCF and non-adherent cells are transferred to the new tissue culture plate, plastic-adherent population is discarded. Volume of media is adjusted as needed to maintain less then a million cells/ml. Cells are cultured under these conditions for 5-15 weeks.

Cells cultured in 10% FBS containing media become 10-20% mast cells by week 5 and maintain that number of mast cells at least through week 15. Cells cultured in 2% BSA containing media become >80% mast cells and can be utilized for BioMap assays at week 5 of culture, cells cultured in other media become >80% mast cells and can be utilized for BioMap assays at week 9-10 of culture. At the end of culture mast cell are induced for 1-2 weeks in media supplemented with 10% FBS, and 20 ng/ml IL-4±5 µg/ml human IgE alone or together in combinations. Agents for mast cell induction may also include IL-6, SCF, IgG, superoxides, complement proteins (C5a), neuropeptides (Substance P) and lipoproteins (At the end of culture mast cell are induced for 1-2 weeks in media supplemented with 10% FBS. Induced mast cells are incubated with 10 mg/ml human IgE for 2-12 hours at 37° C. prior to addition to the BioMap assay. IgE-labeled mast cells are seeded into 96-well plates onto confluent HUVEC at 5–20×10$^3$ cells/well in EGM-2 media. Mature mast cells are seeded into 96-well plates onto confluent HUVEC, UASMC or combination of HUVEC and UASMC at 5–20×103 cells/well in EGM-2 media or SmGM-2 media.

Primary human umbilical vein endothelial cells (HUVEC) are used. Other cells that may replace HUVEC in the screen include primary microvascular endothelial cells, aortic or arteriolar endothelial cells. 2×10$^4$ cells/ml are cultured to confluence in EGM-2 (Clonetics). Other media that may replace EGM-2 include EGM (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984).

Primary human umbilical artery smooth muscle cells (UASMC) are used. Other cells that may replace UASMC in the screen include primary aortic, bronchial, coronary artery or pulmonary artery smooth muscle cells; cardiomyocytes or skeletal muscle cells. Passage 5-7 cells are used for the screen. 4×10$^4$ cells/ml are cultured to 80% confluence in SmGM-2 (Clonetics) containing 5% FBS. In some cases, SmGM-2 may be removed 24 hours before screen, and replaced with serum-free SmBM basal media (Clonetics) supplemented with insulin.

Test agents or buffer controls are added and mast cells cocultures are stimulated with ng/ml IL-4 and 20 µg/ml goat anti-human IgE or 20 µg/ml of anti-human IgG (Sigma) or 0.1-1 µM C5a (Sigma) or 1 µM A23187 (Sigma) or 3 µg/ml Compound 48/80 (Sigma) or NP-BSA (Biosearch Technologies, Inc.) or 5 µg/ml Concavalin A (Sigma) or LPS. Additional stimulators of interest for mast cell cocultures may include IL-1beta, pertussin toxin, lipoproteins, superoxides, C3a and other complement system components, neuropeptides (Substance P, epinephrine), TLR2 and TLR4 activators (LPS, zymosan, bacterial peptidoglycan) and adenine nucleotides (ATP, ADP and UTP). After 24 hour, cultures are evaluated for expression of mast cell Tryptase, VCAM-1, CD87, CD62P, ICAM-1, IL-8, Eotaxin-3, CD55, VEGFR2, Endothelin-1, PAI-1 and MCP-1. Other markers of interest may include mast cell chymase, heparin proteoglycan, CD142, CD69, CD62E, PAR2, IL-1a, CD59, HLA-DR, CD117, IL-4, IL-5, IL-6, IL-13, GM-CSF, tPA, fibronectin, vitronectin, Collagen I, MMP-1, MMP-2, MMP-9 and PDGF.

Example 9

Adipocyte Biomaps

Primary human adipocytes are used. Mature human adipocytes are derived from visceral or subcutaneous preadipocytes (Cambrex or Cell Applications) or from human mesenchymal stem cells (MSC, Cambrex).

Preadipocytes are cultured in Preadipocyte Growth Medium (PGM, Cambrex) supplemented with 10% FBS, 2 mM 1-glutamine, 100 U/ml of Penicillin and 100 ug/ml of Streptomycin to 70% confluency. Passage 1-2 preadipocytes are used for adipocyte differentiation and screening. 1-5× 10e5 cells/well of 96-well plate are seeded in Preadipocyte Differentiation Media (PDM, Cambrex) supplemented with 10 ug/ml insulin, 1 uM dexamethasone, 200 uM indomethacin and 500 uM isobutylmethylxanthine. Lipid vacuoles in differentiating adipocytes will begin to appear 4-5 day after induction of differentiation and will continue to increase in number and size for 7-10 days. Test agents and stimuli may be applied at different time during this cultures. Dexamethasone and indomethacin may be removed to screen agents that induce adipocyte differentiation. Oil Red O may be used to determine efficiency of adipocyte differentiation.

MSC are cultured in Mesenchymal Stem Cell Growth Media (MSCGM, Cambrex) to 90% confluency. Passage 5-7

MSC are used for adipocyte differentiation and screening. 5–10×10e3 cells/well of 96-well plate are seeded in MSCGM and cultured until 100% confluency. Adipocyte differentiation is induced by three cycles of induction/maintenance consisting of culturing MSC in Adipogenesis Induction Medium for 3 days followed by culture in Adipogenesis Maintenance Medium. Following three cycles of induction/maintenance, adipocytes are cultured for additional 7 days in Adipogenesis Maintenance Medium.

Test agents or buffer controls are added and adipocyte cultures are stimulated with combinations of TNF-a, IL-11, leptin, glucose, insulin, or adiponectin. Additional stimulators of interest for adipocyte cultures may include angiotensin-II, IL-1beta, TGFbeta, glucogon, lipoproteins, CRP, and TLR2 and TLR4 activators (LPS, zymosan, bacterial peptidoglycan). After 24 hour, cultures are evaluated parameters such as VCAM-1, IL-8, MCP-1, TNF-a, glucose, IP-10, MIG, M-CSF, LDL-R, IL-6, leptin, CRP, serum amyloid A, adiponectin, glucose, resistin, pentraxin-3, HDL, LDL, apolipoproteins, IL-11, TGFb, MMP-1, MMP-9, TIMP-1, TIMP-2, and IGF-1.

Example 10

Adipocyte/EC BioMAPs

Primary human adipocytes are used. Mature human adipocytes are derived from visceral or subcutaneous preadipocytes (Cambrex or Cell Applications) or from human mesenchymal stem cells (MSC, Cambrex).

Preadipocytes are cultured in Preadipocyte Growth Medium (PGM, Cambrex) supplemented with 10% FBS, 2 mM I-glutamine, 100 U/ml of Penicillin and 100 ug/ml of Streptomycin to 70% confluency. Passage 1-2 preadipocytes are used for adipocyte differentiation and screening. 1-5×10e5 cells/well of 96-well plate are seeded in Preadipocyte Differentiation Media (PDM, Cambrex) supplemented with 10 ug/ml insulin, 1 uM dexamethasone, 200 uM indomethacin and 500 uM isobutylmethylxanthine. Lipid vacuoles in differentiating adipocytes will begin to appear 4-5 day after induction of differentiation and will continue to increase in number and size for 7-10 days. Test agents and stimuli may be applied at different time during this cultures. Dexamethasone and indomethacin may be removed to screen agents that induce adipocyte differentiation. Oil Red O may be used to determine efficiency of adipocyte differentiation.

MSC are cultured in Mesenchymal Stem Cell Growth Media (MSCGM, Cambrex) to 90% confluency. Passage 5-7 MSC are used for adipocyte differentiation and screening. 5–10×10e3 cells/well of 96-well plate are seeded in MSCGM and cultured until 100% confluency. Adipocyte differentiation is induced by three cycles of induction/maintenance consisting of culturing MSC in Adipogenesis Induction Medium for 3 days followed by culture in Adipogenesis Maintenance Medium. Following three cycles of induction/maintenance, adipocytes are cultured for additional 7 days in Adipogenesis Maintenance Medium. Cells are harvested and resuspended to $10^6$ cells/ml and added to confluent endothelial cells.

Primary human umbilical vein endothelial cells (HUVEC) are used. Other cells that may replace HUVEC in the screen include primary microvascular endothelial cells, aortic or arteriolar endothelial cells. $7.5 \times 10^4$ cells/ml are cultured to confluence in EGM-2 (Clonetics). Other media that may replace EGM-2 include EGM or EGM-2MV (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984).

Test agents or buffer controls are added and adipocyte/endothelial cell co-cultures are stimulated with combinations of TNF-alpha, IL 1β, IFNγ, IL-11, glucose, insulin. Additional stimulators of interest for adipocyte cultures may include angiotensin-II, TGFβ, glucogon, lipoproteins, CRP, IL-4, histamine, and TLR2 and TLR4 activators (LPS, zymosan, bacterial peptidoglycan). After 24 hour, BioMAPs are gemerated with the following parameters E-selectin, VCAM-1, IL-8, MCP-1, MIP1alpha, IP-10, IL-1, MIG, M-CSF, LDL-R, tissue factor, thrombomodulin, PAI1, VEGFR-2, Eotaxin-3, adiponectin, resistin, and uPAR. Other parameters of interest include TNF-αc, glucose, R, IL-6, leptin, CD40, CD69, CRP, serum amyloid A, pentraxin-3, GLUT4, tPA, uPA, TNFRI, II, TGFbR-1, 2, 3, HDL, LDL, apolipoproteins, IL-11, TGFβ, MMP-1, MMP-2, MMP-9, MMP-11, TIMP-1, TIMP-2, VEGF and IGF-1.

Example 11

Multiple Systems Analysis

The present invention is applied for the screening of compounds for use in treating vascular dysfunction associated with cardiovascular disease, hypertension, diabetes and autoimmune disease.

Test agents are evaluated in HDF-3C/TGF, HUVEC/M-Zym, SMC-3C, HU3C, HUPBMC-LPS, and HUPBMC/SAg systems.

A database of biomaps is generated from this panel of assay combinations for test agents that include known cardioprotective agents including beta blockers and other hypertensive drugs, ACE inhibitors, AT1 antagonists, and anti-aldosterones; statins; and others, are screened and a biomap generated that shows the changes in the markers with the different anti-cancer agents. Such compounds are given in The Pharmacologic Basis of Therapeutics. The biomaps with the known agents are used to compare to candidate cardioprotective drugs. This allows the recognition of the pathway(s) the candidate drug acts on, by comparing the changes in the level of the specific markers for known drugs affecting known pathways and the changes observed with the candidate drug. In addition to further add to the utility of the biomap, one may include in the database reference biomaps generated from assay panels containing cells with genetic constructs that selectively target or modulate specific cellular pathways (e.g. NFκB, MAP kinase, etc), or cells that contain known genetic mutations (e.g. CD36-deficiency, Yanai, Am. J. Med. Genet. 93:299, 2000, etc.).

FIG. 5 shows the BioMAP profile for mycophenolic acid (an inhibitor of IMDPH) Key features of the mycophenolic acid profile are inhibition of MCP-1 in the 3C, SAg, LPS, Mphg, and SM3C systems. MCP-1 plays a role in the recruitment of monocytes into inflammatory sites, including vascular inflammatory sites. Mycophenolic acid is a treatment for heart and kidney transplant. Mycophenolic acid, unlike many other immunosuppressants, has long-term benefits in heart transplant patients, protecting against post-transplant vasculopathy. (Keogh, A., 2005, Transplantation, 79:S45; Valentine, H., 2004, J. Heart Lung Transplant 23:S187)

What is claimed is:

1. A method comprising:

contacting an agent with two or more cell culture systems selected from the group consisting of:
   (a) human neonatal fibroblasts (HDFn) in the presence of TNF, IFNγ and TGFβ, and measuring the levels of at least three different proteins selected from the group consisting of: ICAM, VCAM, CD40, CD90, IP-10, MCP-1, Collagen I, Mig, m-CSF, TIMP-2, PAI-I, and IL-8, prior to and subsequent to the contacting;
   (b) HDFn in the presence of TGFβ, and measuring the levels of at least three different proteins selected from the group consisting of: CD90, Collagen I, Collagen III, HLA-DR, PAI-I, and VCAM, prior to and subsequent to the contacting;
   (c) primary human artery smooth muscle cells in the presence of TNF-alpha, IL-1, and IFNγ, and measuring the levels of at least three different proteins selected from the group consisting of: VCAM, CD40, HLA-DR, ICAM, IL-8, MCP-1, M-CSF, MIG, Thrombomodulin, serum amyloid A, and uPAR, prior to and subsequent to the contacting; and
   (d) macrophages and endothelial cells cultured in the presence of Toll-like receptor ligands, and measuring the levels of at least three different proteins selected from the group consisting of: CD38, CD40, CD69, E-selectin, IL-8, MCP-1, and MIG, prior to and subsequent to the contacting; and determining changes in protein expression that result from the contacting of said agent, wherein the determining is based on differences between the measured protein levels prior to and subsequent to the contacting;

recording said changes in protein expression.

2. The method of claim 1 further comprising simultaneous analysis of three or four of cell culture system (a), cell culture system (b), cell culture system (c), and cell culture system (d).

3. The method of claim 1 further comprising simultaneous analysis of each of cell culture system (a), cell culture system (b), cell culture system (c), and cell culture system (d).

4. The method according to claim 1, wherein said agent is a genetic agent.

5. The method according to claim 1, wherein said agent is a chemical or biological agent.

6. The method according to claim 1, wherein a plurality of cell culture systems are concatenated for simultaneous analysis.

* * * * *